United States Patent [19]
Rudolph et al.

[11] Patent Number: 5,488,267
[45] Date of Patent: Jan. 30, 1996

[54] XENON LAMP SYSTEM FOR MATERIALS TESTING APPARATUS

[75] Inventors: Bernd Rudolph, Alzenau; Klaus J. Dietz, Wiesbaden; Klaas Oostlander, Hanau, all of Germany

[73] Assignee: Heraeus Xenotest GmbH, Hanau, Germany

[21] Appl. No.: 280,311

[22] Filed: Jul. 26, 1994

[30] Foreign Application Priority Data

Aug. 2, 1993 [DE] Germany .................... 43 25 718.6

[51] Int. Cl.⁶ .................................................. H01J 7/44
[52] U.S. Cl. ........................ 315/63; 315/291; 250/492.1
[58] Field of Search ........................ 315/246, 115, 315/291, 307, 32, 56, 63; 250/492.1

[56] References Cited

U.S. PATENT DOCUMENTS

| | | | |
|---|---|---|---|
| 3,686,940 | 8/1972 | Kockott | 73/150 |
| 4,747,645 | 8/1988 | Rudzki | 350/1.1 |
| 4,884,009 | 11/1989 | Rothwell | 315/246 |

FOREIGN PATENT DOCUMENTS

| | | |
|---|---|---|
| 0320974 | 6/1989 | European Pat. Off. . |
| 2139860 | 1/1973 | France . |
| 0139860 | 1/1973 | France . |
| 1589419 | 7/1970 | Germany . |
| 2120717 | 11/1972 | Germany . |
| 3636901 | 5/1988 | Germany . |
| 3636901A1 | 5/1988 | Germany . |
| 2752593 | 12/1988 | Germany . |

OTHER PUBLICATIONS

Jurgen Kiefer, Ultraviolette Strahlen, pub. 1977 by Walter de Gruyter Co., Berlin & New York, p. 95, table 3.12.
Heraes Original Hanau Division, Xenotest 1200 brochure No. D310561/3C 6.89/N.Ko, published Jun. 1989, 8 pages.

*Primary Examiner*—Robert J. Pascal
*Assistant Examiner*—Reginald A. Ratliff
*Attorney, Agent, or Firm*—Frishauf, Holtz, Goodman, Langer & Chick

[57] ABSTRACT

An illumination system for weathering and fading resistance test instruments is provided with a pulse-driven xenon gas discharge lamp with an elongated discharge bulb that has an electrode spacing in the range from 10 to 50 cm; by adjusting the duty factor of the lamp current by means of an electronic control unit, a predetermined ratio between ultraviolet and infrared radiation is achieved; for the sake of light density, the lamp bulb is bent in a U.

9 Claims, 5 Drawing Sheets

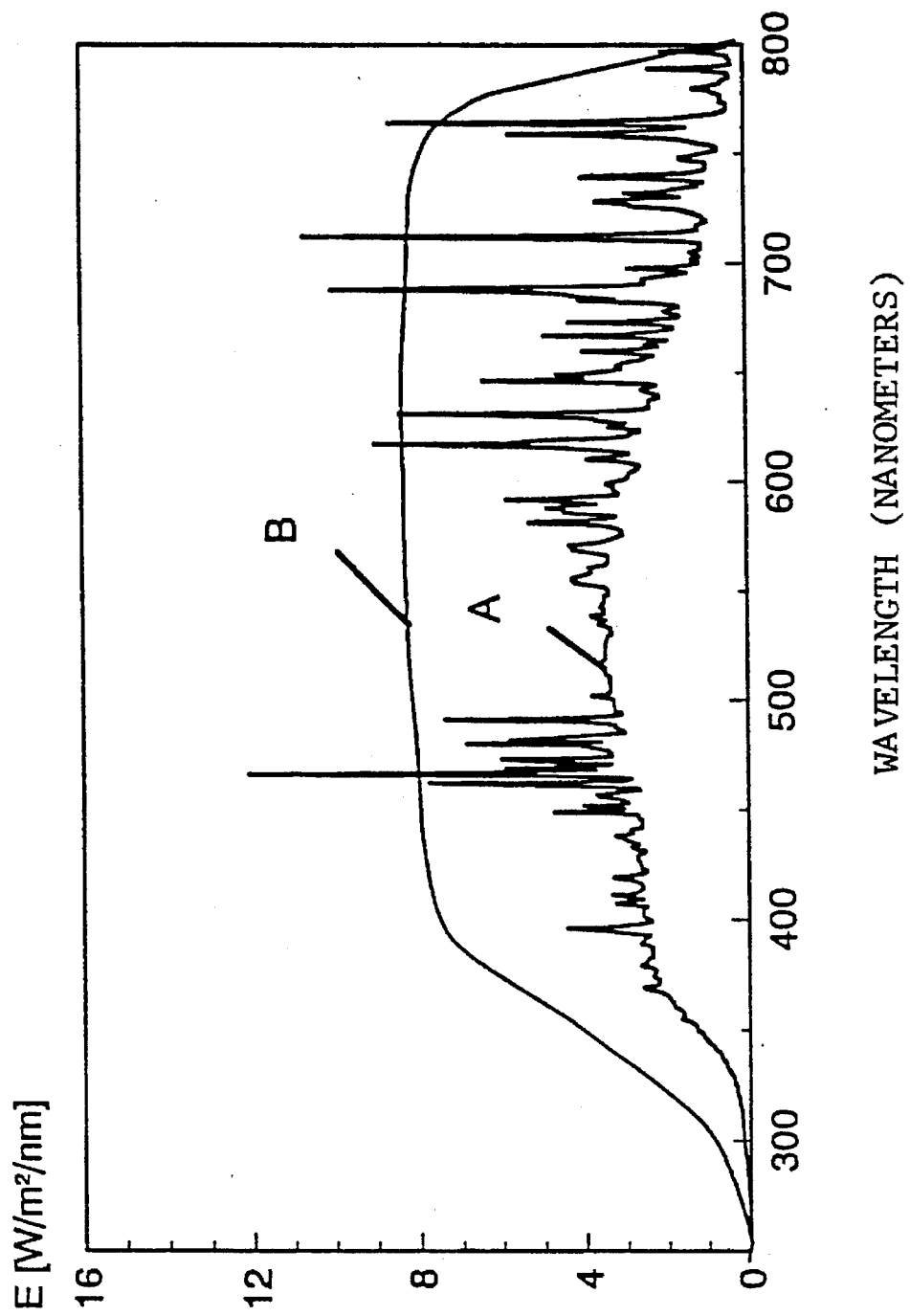

XENON LAMP SYSTEM FOR MATERIALS TESTING APPARATUS

CROSS-REFERENCE TO RELATED PATENTS AND APPLICATION, THE DISCLOSURE OF WHICH ARE HEREBY INCORPORATED BY REFERENCE

U.S. Pat. No. 3,686,940, Kockott, Aug. 1972;

U.S. Pat. No. 4,747,645, Rudzki;

U.S. Pat. No. 4,884,009, Rothwell & Grant, Nov. 28, 1989.

CROSS REFERENCE TO RELATED LITERATURE

"Ultraviolete Strahlen" [Ultraviolet Radiation], Jürgen Kiefer, ed., Verlag Walter de Gruyter, Berlin and New York, 1977; Heraeus Brochure No. D 310 561/3C 6.89/N Ko, pub. June 1989.

FIELD OF THE INVENTION

The invention relates to an illumination system for weathering and fading resistance test instruments having a xenon gas discharge lamp. The lamp has an elongated lamp bulb that has one electrode at each of its ends, between which electrodes an arc discharge burns; the lamp is operated in a pulsed mode by means of an electronic control unit that has a controllable switch.

BACKGROUND

U.S. Pat. No. 4,747,645, RUDZKI a weathering and fading resistance test instrument which provides for accurate adjustment of a defined radiation spectrum that encompasses ultraviolet (UV) radiation, infrared (IR) radiation and visible light, by means of a xenon radiation source. The system has at least two sectors from which the radiation emerges: UV mirrors that are impermeable to UV radiation, as well as a UV filter and at least one IR filter that are permeable to visible light. Each of the sectors is associated with one xenon radiation source; the filter/radiation source system is surrounded first by a quartz inner cylinder with a selectively reflective layer for IR that is permeable to UV and visible light, and an adjacent water jacket which absorbs long-wave IR radiation, then by a quartz outer cylinder, and finally by a three-piece sealing jacket made of US special glass or window glass. By means of this illumination system, it is possible to damp the intensity of given spectral components in a targeted fashion, or to vary and set the ratio of the ultraviolet to the infrared components purposefully, which is especially important for materials testing.

It is also known from the book entitled "Ultraviolete Strahlen" [Ultraviolet Radiation] edited by Jürgen Kiefer and published by Verlag Walter de Gruyter, Berlin and New York, 1977, page 95, to purposefully adjust the spectral light yield of flash units for cameras and the like with a xenon filling by specifying not only the gas pressure discharge duration, but also electrical parameters such as the arc length, voltage applied, and current density. Page 90 of this same book, in the next-to-last paragraph, refers to wall-stabilized lamps for pulsed mode operation, which are suitable for materials testing and mounting. As the second paragraph on page 90 says, it is essential that the xenon discharge lamp not require any burn-in time, or in other words that it reach its full power immediately after firing; for these reasons, xenon lamps are easily modeled or used as flash units.

It is also known from the corporate brochure No. D 310 561/3C 6.89/N Ko, published 1989 by W. C. Heraeus GmbH and captioned "XENOTEST 1200 CPS," to simulate natural sunlight by means of radiation source/filter systems; page 5 of this brochure indicates the spectral energy distribution of the illumination system in comparison with global (natural solar) radiation.

U.S. Pat. No. 4,884,009, ROTHWELL & GRANT, discloses an argon gas discharge lamp in which the emission color is related directly to the duration of the current pulse. Current pulses shorter than 5 microseconds and preferably 1 microseconds are described at col. 2, line 54, as well as so-called long-current pulses between 5 and 10 microseconds; the short pulses tend to produce a glow discharge, while the long pulses produce a transition from the glow discharge to arc discharge; however, the other parameters such as the fill pressure, doping materials and filling gas are also jointly responsible for the radiation emitted. Nevertheless, this patent does not teach any possibilities for utilizing predetermined spectral components for test instruments.

THE INVENTION

An object of the present invention is to provide a space-saving illumination system with a discharge lamp having a predetermined ratio of ultraviolet to infrared radiation; the discharge lamp should require no burn-in time and should have a rapid turn-off time. The illumination system is intended for use in materials testing equipment with a high energy yield.

Briefly, the electrode spacing defining the arc length is in the range from 10 to 50 cm; the inside diameter of the bulb is in the range from 5 to 15 mm; the duty factor is in the range from 1:1 to 1:100; and the amplitude values of the discharge current are in the range between 15 and 100 A at a cold fill pressure of less than 400 mbar.

In a preferred embodiment, the lamp bulb comprises a U-shaped discharge tube, whose ends each have an electrode. The small structural form proves advantageous in this respect for the low-pressure radiation source, while preserving the requisite arc length and achieving high illumination density.

In a preferred embodiment, the discharge current comprises pulses of alternating polarity, and the maximum duration of the current pulses is 10 ms. The uniform heating of both electrodes proves advantageous in this respect.

As an electronic control unit, an alternating current final control element is used, which is provided either with two anti-parallel-connected thyristors or a triac. The electronic control is preferably connected to an alternating voltage power grid, and the pulse train frequency of the discharge current corresponds to the grid frequency. It proves to be advantageous that a commercially available device such as a dimmer can be used here.

The subject-matter of the invention is described in further detail below in conjunction with drawing FIGS. 1, 2a, 2b, 2c, 2d, 2e, 2f and 3.

DRAWINGS

FIG. 1a schematically shows a xenon discharge lamp, bent in a U, in a materials testing instrument, with a mount, shown in part, for the material samples; for the sake of simplicity, the housing wall, sample holder and lamp connection are shown partly cut away;

FIG. 1b is a longitudinal section through the system shown in FIG. 1a;

FIG. 3 shows the spectral energy distribution of the radiation produced, which is filtered in accordance with the aforementioned Heraeus brochure D 310 561/3C 6.89/N Ko.

DETAILED DESCRIPTION

Figure 1A:
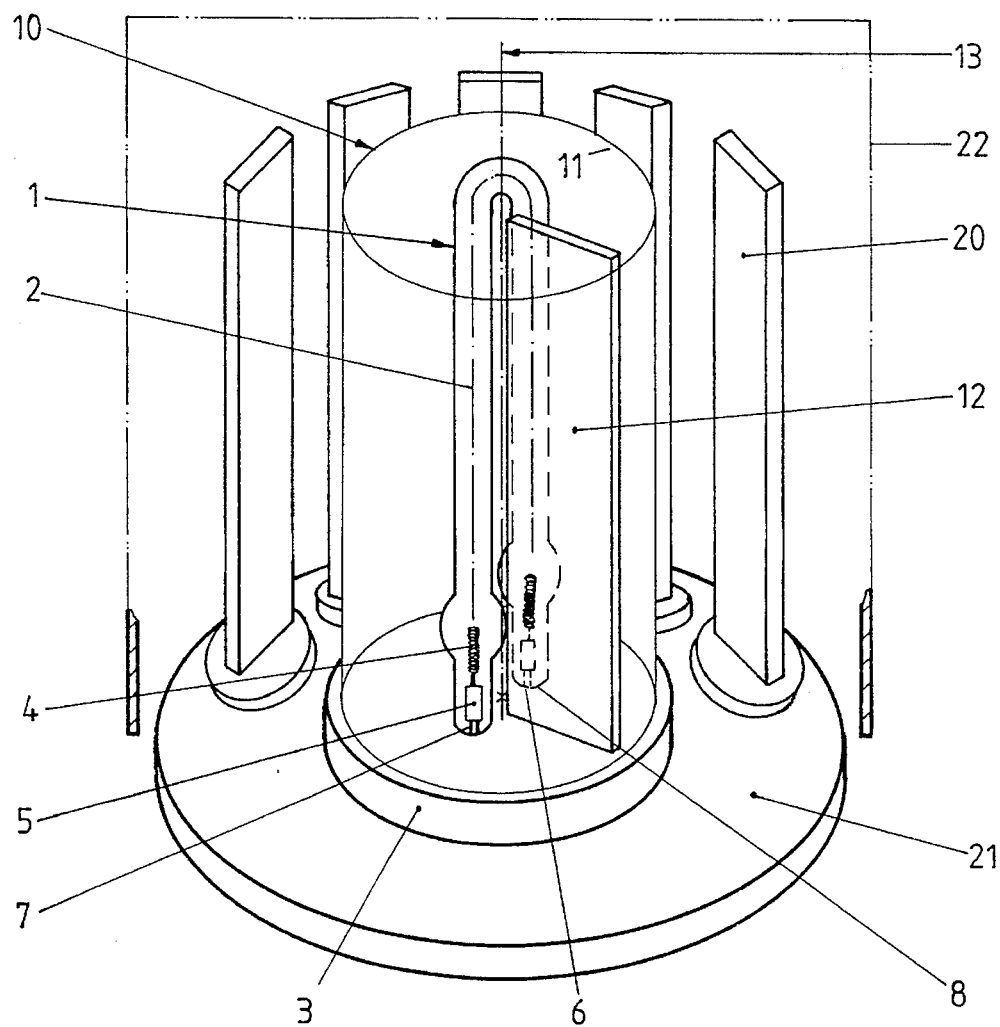

In FIG. 1, the xenon discharge lamp 1, bent in a U, is located with its U-shaped tubular discharge chamber 2 on a base plate 3; each of the ends of the U-shaped lamp bulb 2 has a respective electrode 4, whose current leadthroughs 5 and 6 pass in a sealed manner through the tube ends 7 and 8 of the bulb and are electrically and mechanically firmly mounted with contacting mounts inside the base plate 3.

The base plate 3 serves to support an annular filter 10, which is permeable to the ultraviolet (UV) radiation desired for materials testing and to visible light, while the infrared (IR) radiation also generated by the discharge lamp is reflected, by means of an interference coating 11 applied to the inside of the annular filter, onto a plate-shaped absorber 12 located in the interior of the annular filter; the absorber 12 is connected to a cooling device, which however is not shown here for the sake of simplicity.

The base plate is surrounded by a plurality of sample holders 20, which are attached to a rotor 21 that is rotatable concentrically around the annular filter 10. In order to achieve special atmospheric conditions in the region of the samples, it is possible to seal off the sample chamber from the outside world by means of a surrounding housing 22; the current leadthroughs 5 and 6 of the lamp ends 7 and 8 are inserted atmospherically tightly inside the base plate, or optionally the lamp 1 is surrounded by a housing, not shown here for the sake of simplicity, such as a sealed-off annular filter, which keeps the atmospheric conditions prevailing within the sample chamber away from the lamp and its connections. Depending on requirements, such atmospheric conditions can be simulated in the sample chamber or in a sector, and the material samples are exposed to different climatic zones in succession as the particular sample holder passes through them; it is possible to have the radiation act continuously upon the sample.

Figure 1B:
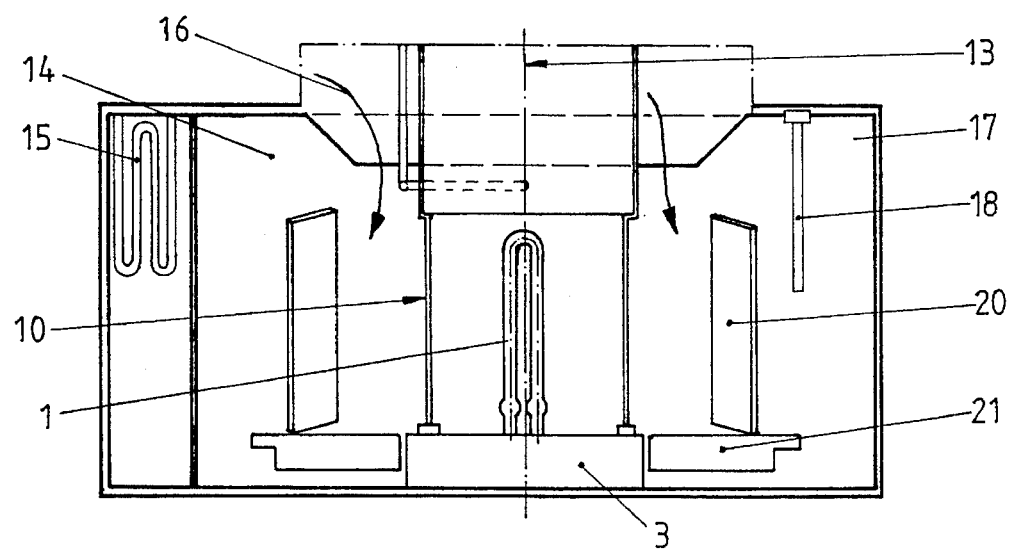

It can be seen from the schematic system shown in FIG. 1b that a sectoral region 14 is provided with a heater device 15 and a moistening device 16, while the diametrically opposed sectoral region 17 is provided with a sensor device 18 that serves to ascertain the temperature, humidity and radiation intensity, and that is optionally used for gas analysis of the specimen chamber atmosphere.

Because of the differing radiating characteristic of the U-shaped lamp 1, it has proved to be especially advantageous, for the sake of uniform illumination of the samples, to have them rotate continuously, by means of the rotor 21, about the fixed base plate with the discharge lamp 1; again, for the sake of simplicity, the drive mechanism involved is not shown.

One essential characteristic of the invention is considered to be that the test instrument can be made extraordinarily compact in form, even though offering high radiation intensity; because of the pulsed mode operation and the associated parameters, such as the arc length, current density, and cold filling pressure, a very specific spectrum can be purposefully established, and this is especially effective for the aging of the material samples. The requisite circuit arrangement for this purpose will be described in conjunction with the following drawings.

Figure 2A:
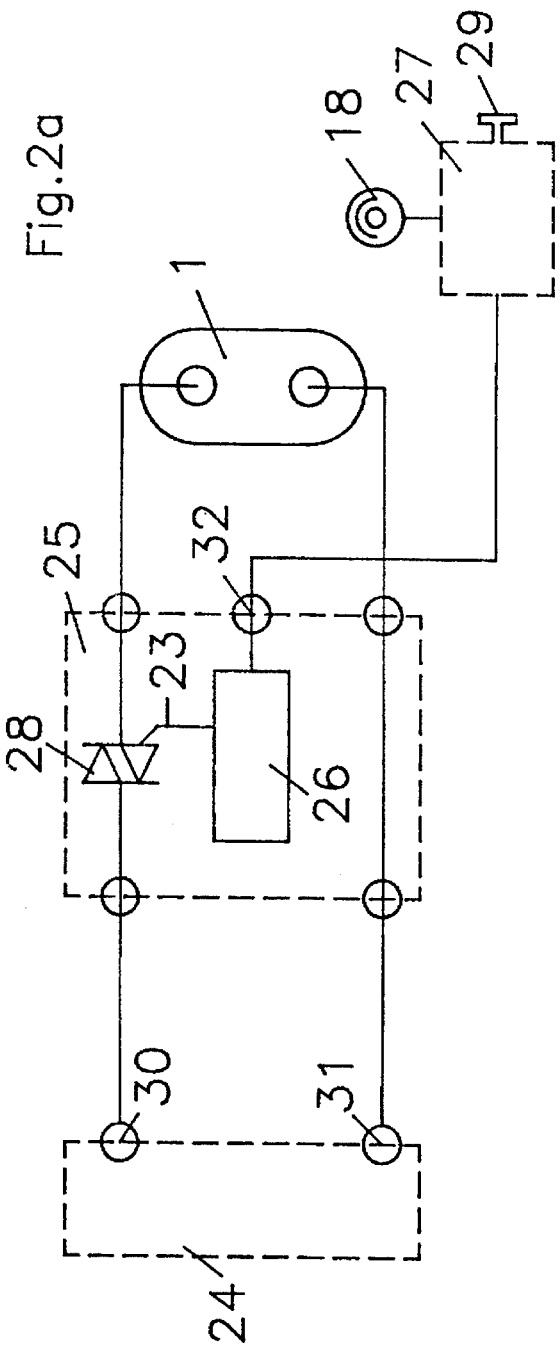
FIGS. 2a, 2b, 2c, 2d, 2e and 2f show alternating current final control elements in various embodiments for operation of the discharge lamp.

FIG. 2a shows the energy supply of a radiation source 1, which is supplied with power via the terminals 30, 31 of a power supply 24 from an alternating current final control element 25, which in turn is triggered by a control unit 26. A control device or regulator 27 is connected to the control input 32 of the control unit 26 and is provided with a photosensor 18 as an instantaneous or actual value transducer and with a fine adjustment device 29; when the control device is used as a regulator, the fine adjustment device 29 serves as a command value transducer for the desired spectrum. It will be appreciated that it is also possible, in a simplified form, to operate the control device 27 without a regulating function; in that case, the photosensor as the actual value transducer is dispensed with, and the adjustment of the radiation originating in the lamp 1 is done via the fine adjustment device 29. The use of a triac 28, which is connected directly to the control unit 26 via the terminal 23, as an electronic switch inside the alternating current final control element 26, has proved especially practical.

Figure 2B:
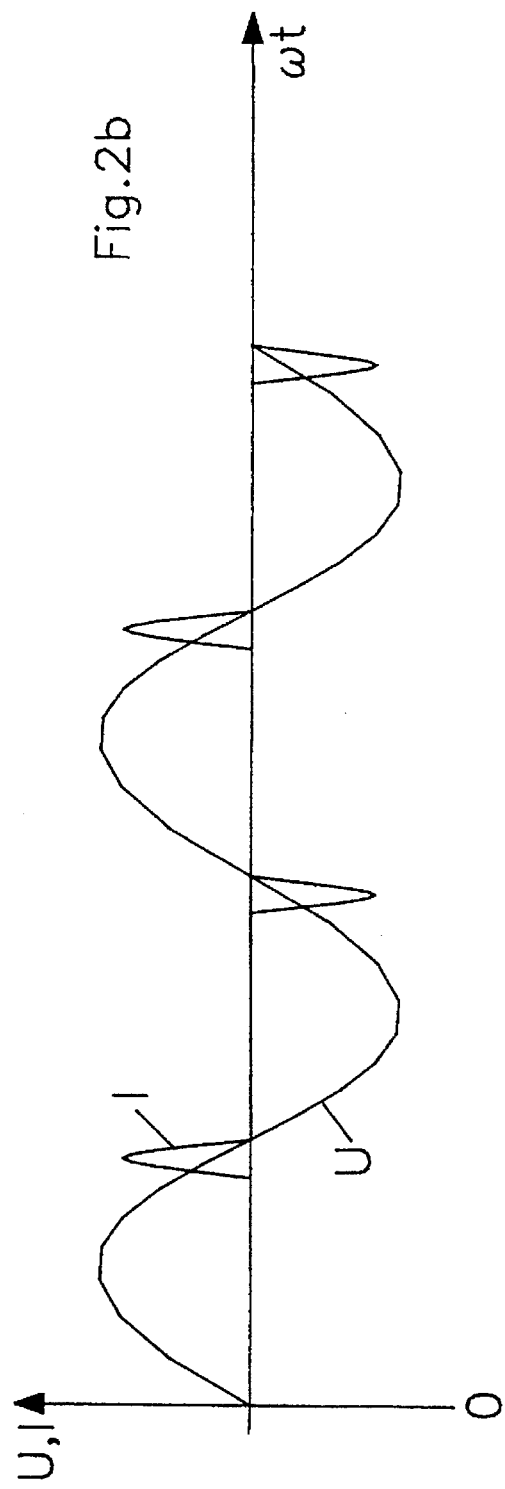

As can be seen from the associated current/voltage timing diagram of FIG. 2b, the triac 28 inside the alternating current final control element is triggered periodically by the control unit 26 in such a way that, by phase-shift control, current I flows within the range from 160° to 180° and from 340° to 360° of the voltage curve U. By means of the fine adjustment device 29, shown symbolically, of the control device 27 connected to the control unit 26, the phase-shift is adjusted such that a desired UV spectral component in the range from 200 to 400 nm, as is required for the particular material sample, results.

As already mentioned above, however, it is also possible for the spectrum output by the lamp 1 to be picked up by the photosensor 18 and delivered to the control device 27 serving as a regulator, which readjusts the control unit, by comparison with a spectral command-value transducer, until such time as the spectrum generated by the command-value transducer matches the actual value output by the lamp. Supply by the alternating current final control element 25 takes place in the present case via the terminals 30, 31 of the power supply unit or alternating current grid connection. It is also possible, however, to use a separate alternating current generator. In the exemplary embodiment shown by FIGS. 2a, 2b, the maximum current intensity is 12 A, and the voltage applied to the radiator is 115 V, and the arc has a length of 280 mm. The cold filling pressure of the xenon radiation source 1 is in the range from 100 mbar to 400 mbar. Naturally, it is possible to increase the UV spectral component still further by means of additional doping materials, such as tin iodide ($SnI_2$).

Figure 2C:
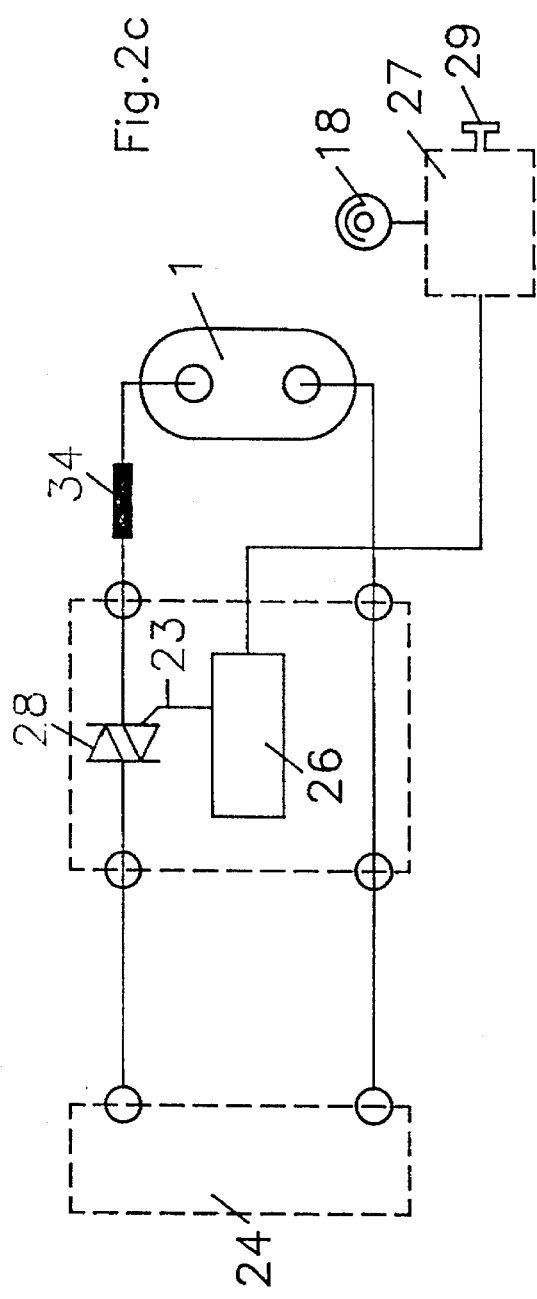
Figure 2D:
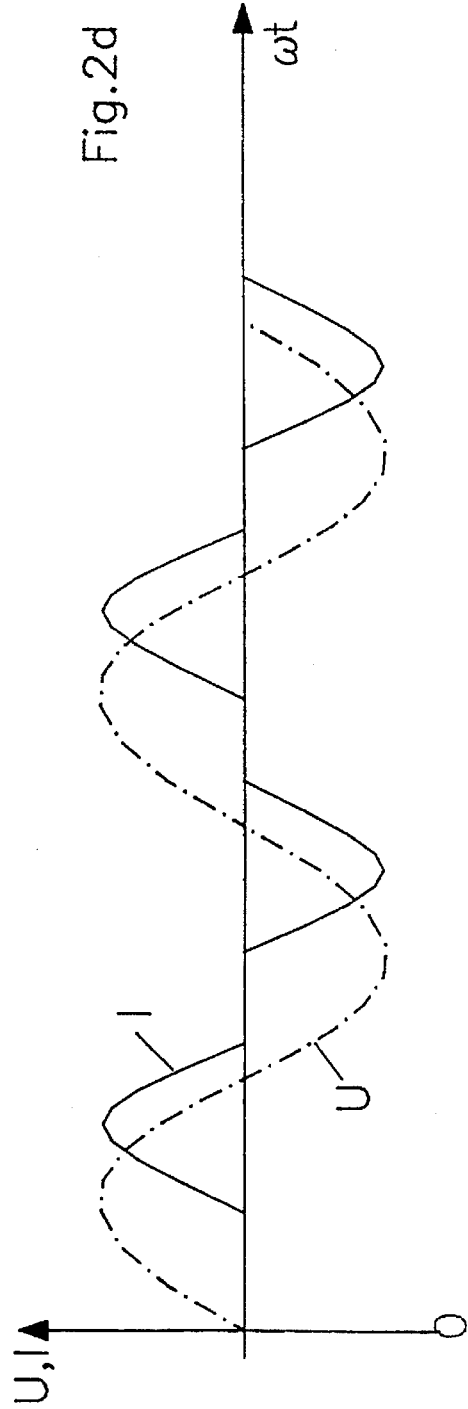

As shown in FIG. 2c and the current/voltage diagram 2d, it is also possible to drive the radiation source 1 with a relatively low voltage of, for example, 65 V; the firing angles of the current I are in the range from 85° to 90° and 165° to 180° of the voltage curve U, and a maximum current density of 35 A is achieved; triggering of the control unit is done analogously with FIG. 2a. The inductance 34 serves the purpose of current limitation.

Figure 2E:
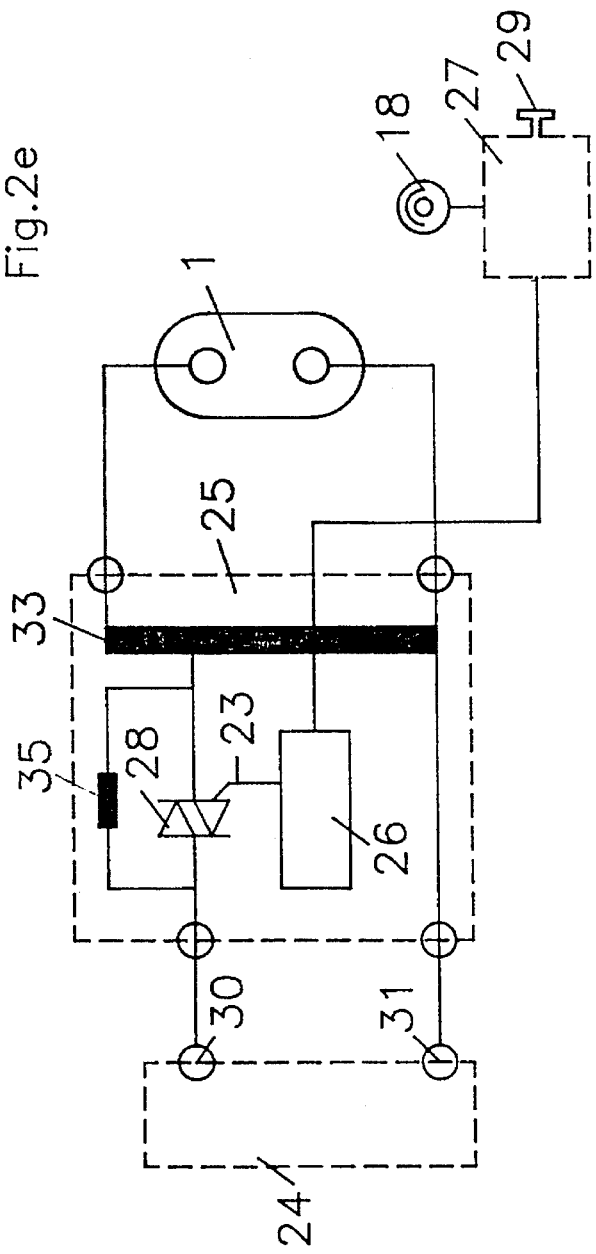
Figure 2F:
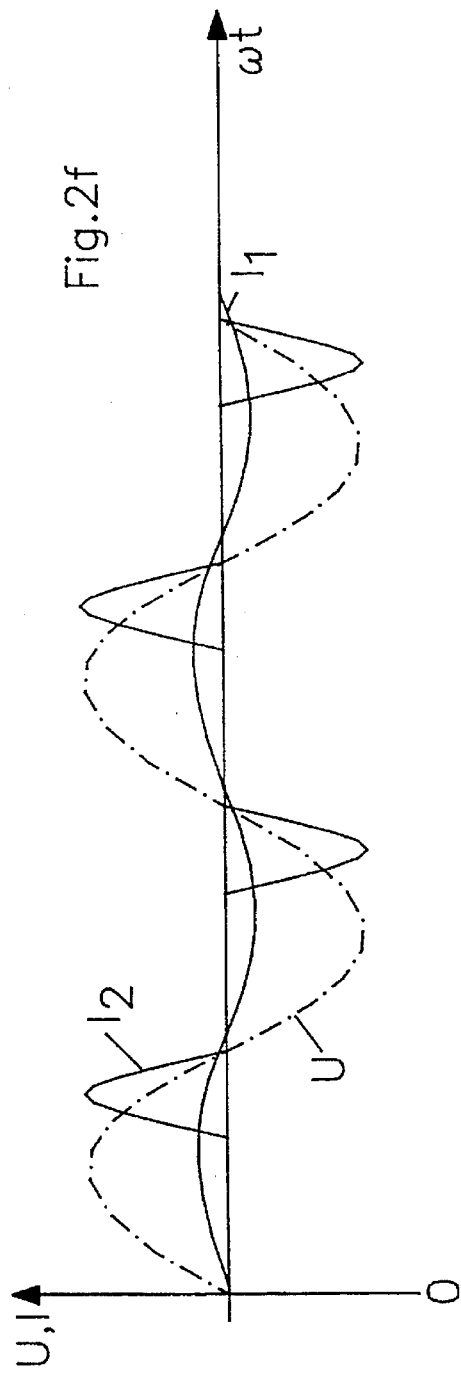

As shown in FIG. 2e, it is possible, by using an autotransformer 33 connected to the alternating current final control element 25, to raise the voltage of the radiation source 1 so that it is on the order of magnitude of 390 V. The circuit arrangement of the control unit 26 and control device or regulator 27 corresponds in principle to that described in conjunction with FIGS. 2a and 2c. As the associated current/voltage timing diagram of FIG. 2f shows, via an inductance 35 connected parallel to the triac 28, a fundamental current $I_1$ with a maximum amplitude of 7 A is generated that is in phase with the voltage U, and on which a current $I_2$, flowing via control electronics by means of phase-shift control, is superimposed. The firing angle of the maximum 16 A current is in the range from 85° to 95° or 175° to 185°; once again, the alternating current final control element 25 is connected directly to the terminals 30, 31 of the power supply. Once again, it is possible, by means of a fine adjustment device 29, to adjust the desired spectral range exactly by means of a shift in the phase-shift or phase-chopping angle; however, as already described above, it is also possible to provide a sensor 38 acted upon by the radiation, whose spectral components detected in the UV range are compared with a command or target value and delivered to the control electronics via a regulator.

FIG. 3 schematically shows the improved spectral energy distribution of the illumination system of the invention in accordance with curve B, compared with the conventional distribution of xenon radiation sources represented by curve A; as curve B shows, the UV range of high intensity extends from approximately 200 to 400 nm, and the infrared range extends from 700 to 800 nm.

Various changes and modifications may be made, and features described in connection with any one of the embodiments may be used with any of the others, within the scope of the inventive concept.

A suitable triac 28 is model BTA 40-700 available from the firm ST-SGS Thomson.

A suitable control unit 26 is model TCA 785 available from the firm Siemens.

A suitable control device 27 is model LT7074 available from the firm Linear Technology.

We claim:

1. In and for combination with a test instrument which tests materials with respect to weathering and fading when exposed to light, an illumination system for said weathering and fading resistance test instrument comprising means for generating said light with a predetermined ratio of ultraviolet (UV) to infrared (IR) radiation, said light generating means including a xenon gas discharge lamp (1) having an elongated lamp bulb (2) that has one electrode (4) at each of its two ends, between which electrodes (4) an arc discharge forms, and a fill including Xenon within said bulb (2) and an electronic control unit (25) that has a controllable switch (28), connected to and applying pulses of current across said electrodes (4), thereby creating said arc discharge, wherein the spacing of said electrodes (4) in the lamp defines an arc length which is in the range from 10 to 50 cm; the inside diameter of the bulb (2) is in the range from 5 to 15 mm at said range of the arc length;

the cold fill pressure of said xenon inside said bulb (2) is less than 400 mbar;

the duty factor of the pulses provided by said control unit (25) is in a range from 1:1 to 1:100; and the amplitude values of the discharge current of the pulses are in the range between 15 and 100 A.

2. The illumination system of claim 1, wherein the period length of each current pulse is in the range between about 0.5 milliseconds and about 500 milliseconds.

3. The illumination system of claim 1, wherein the lamp bulb (2) comprises a tube bent at least once intermediate said two ends (7,8).

4. The illumination system of claim 1, wherein the lamp bulb (2) comprises a tube bent in a U, whose ends (7, 8) each have one electrode (4).

5. The illumination system of claim 1, wherein said electronic control device (25) applies pulses of alternating polarity across said electrodes, thereby heating each of said electrodes equally.

6. The illumination system of claim 1, characterized in that the maximum duration of the current pulses is 10 milliseconds.

7. The illumination system of claim 1, characterized in that the electronic control device (25) is an alternating current final control element.

8. The illumination system of claim 1, characterized in that the electronic control unit is connected to an alternating voltage power grid.

9. The illumination system of claim 8, characterized in that the pulse train frequency for the discharge current is equivalent to the frequency of said alternating voltage power grid.

* * * * *